US00PP22161P2

(12) United States Plant Patent
Dirr

(10) Patent No.: US PP22,161 P2
(45) Date of Patent: Sep. 27, 2011

(54) CRAPEMYRTLE PLANT NAMED 'GAMAD VI'

(50) Latin Name: *Lagerstroemia hybrid*
Varietal Denomination: Gamad VI

(75) Inventor: Michael A. Dirr, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 12/800,570

(22) Filed: May 18, 2010

(51) Int. Cl.
*A01H 5/00* (2006.01)

(52) U.S. Cl. ..... Plt./252
(58) Field of Classification Search ..... Plt./252
See application file for complete search history.

(56) References Cited

U.S. PATENT DOCUMENTS

PP17,411 P2 2/2007 Dirr

*Primary Examiner* — Annette Para
(74) *Attorney, Agent, or Firm* — Davis Wright Tremaine LLP

(57) ABSTRACT

A new and distinct cultivar of crapemyrtle, 'Gamad VI', is provided. 'Gamad VI' is a *Lagerstroemia indica*×*Lagerstroemia fauriei* hybrid, which is characterized by compact growth habit, mildew resistance, and early flowering with abundant deep red and purple flowers.

2 Drawing Sheets

Latin name of the genus and species of the plant claimed: 'Gamad VI' is a crapemyrtle plant that is a *Lagerstroemia* hybrid.

Variety denomination: The new crapemyrtle plant claimed is of the variety denominated 'Gamad VI'.

BACKGROUND OF THE INVENTION

The present invention relates to the discovery of a new and distinct cultivar of the ornamental flowering shrub *Lagerstroemia indica*×*Lagerstroemia fauriei*, commonly known as crapemyrtle, and hereafter referred to by the varietal denomination 'Gamad VI', as herein described and illustrated.

The new crapemyrtle originated from open-pollinated seed of 'Pocomoke' (unpatented), a compact, rose-pink flowered introduction in 1999 from the United States National Arboretum (USDA). 'Gamad VI' was derived from plants grown in 2001 at Athens, Ga. from seed collected from open pollinated 'Pocomoke' plants. The seedlings were planted in containers and selections were made at Dearing, Ga. for plants based on the following criteria: 1) compact habit; 2) mildew resistance; 3) early flowering; and 4) flower color and quality. 'Gamad VI' was selected in 2002.

Asexual reproduction by traditional vegetative cuttings since 2002 at Dearing, Ga. has shown that the distinguishing characteristics of this new crapemyrtle variety 'Gamad VI' are stable and reproduced true-to-type in successive generations.

SUMMARY OF THE INVENTION

The new crapemyrtle plant variety 'Gamad VI' has not been observed under all possible environmental conditions. The phenotype may vary somewhat with variations in environment and cultural practices such as temperature and light intensity without, however, any variance in genotype.

The following traits have been repeatedly observed at Dearing, Ga. and are determined to be the unique characteristics of the new crapemyrtle plant variety 'Gamad VI':

1. Compact-mounded habit
2. Mildew resistance

3. Early flowering in late June
4. Abundant deep red and purple flowers

There were no compact purple flowering varieties of crapemyrtle available for comparison. 'Gamad VI' is similar in size to 'Pocomoke', but has larger leaves and is earlier in flowering with abundant deep red/purple flowers compared to the pink flowers of 'Pocomoke'. 'Gamad VI' possesses greater resistance to mildew relative to 'Pocomoke'.

BRIEF DESCRIPTION OF THE DRAWINGS

The accompanying photographic illustrations show typical specimens in full color of the foliage and fruit of the new variety 'Gamad VI'. The colors are as nearly true as is reasonably possible in a color representation of this type.

BOTANICAL DESCRIPTION

Figure 1:
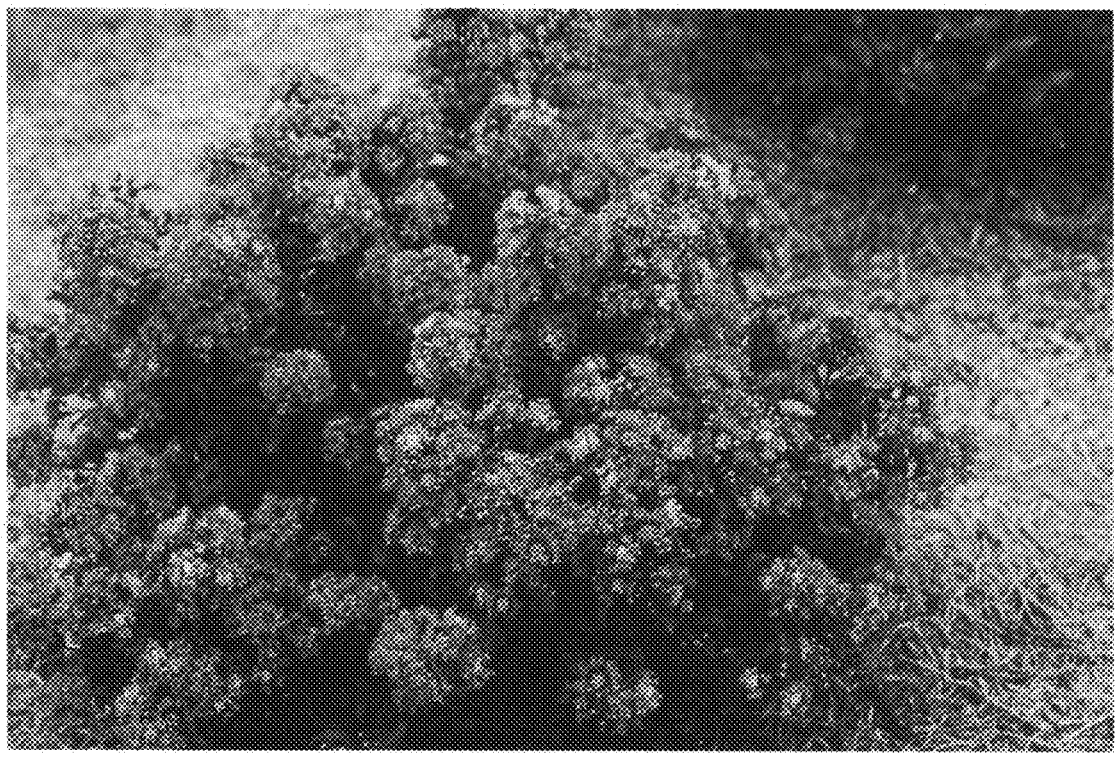
FIG. 1 is a photograph of the new variety 'Gamad VI'.
Figure 2:
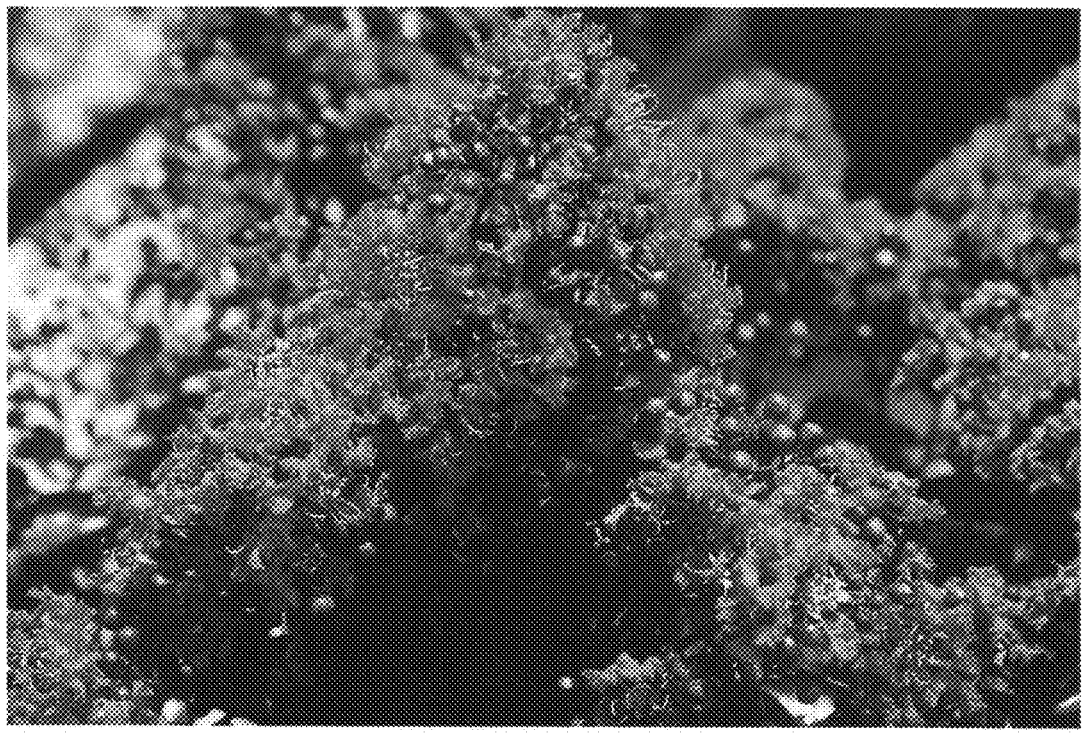
FIG. 2 is a photograph of the fruit and flowers of the new variety 'Gamad VI'.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England.

The following is a detailed description of the botanical and pomological characteristics of the new variety 'Gamad VI'. Where dimensions, sizes, colors, and other characteristics are given, it is to be understood that such characteristics are approximations and averages set forth as accurately as practicable. The descriptions reported herein are largely from specimen plants grown at Dearing, Ga. Data were obtained in August 2006 on plants that were 9 years old.

PLANT

*Habit.*—Upright, more open than other selections, rounded to broad-rounded.

*Size.*—Height: 95 cm. Width: 86 cm.

*Texture.*—Medium.

STEMS

*Color.*—About Greyed-purple RHS 187B in first year, changing to about Greyed-brown RHS N199B in second year.
*Diameter.*—Approximately 2 mm.
*Pubescence.*—Observed along edges.
*Exfoliation.*—None.
*Shape.*—Square.
*Pith.*—Type: Solid. Diameter: Approximately 2 mm. Color: About Green RHS 137A.
*Odor* (*of bruised stem*).—None.
*Lenticels.*—None.
*Internode length.*—Approximately 25 mm to 30 mm.

VEGETATIVE BUDS

*Arrangement.*—Sub-opposite.
*Type.*—Three-scaled, ovoid to rounded.
*Size.*—Length: Approximately 1 mm. Width: Approximately 1 mm.
*Scale number.*—Approximately 3.
*Scale color.*—About Yellow-green RHS 144A.
*Position/disposition.*—Flat against stem.
*Number at node.*—Approximately 2.
*Pubescence.*—Finely hairy along scale edges.
*Shape.*—Ovoid to rounded.

LEAF SCAR

*Shape.*—Raised half ellipse.
*Vascular bundle traces.*—None observed.
*Pubescence.*—None.
*Position of bud.*—Directly on top.
*Color differentiation.*—About Green RHS 137A.
*Size.*—Height: Approximately 1 mm. Width: Approximately 2 mm.

TRUNK OR LARGE STEMS

*Color.*—About Grey-brown RHS 199C.
*Size of stem on which exfoliation begins.*—Approximately 6 mm, with some peeling occurring.
*Diameter.*—Approximately 15 to 18 mm.
*Texture.*—Rough.

LEAF

*Color at emergence.*—Upper: About Yellow-green RHS 148A. Lower: About Yellow-green RHS 148B.
*Color during summer season.*—Upper: About Green RHS 139A. Lower: About Green RHS 137B.
*Mature size.*—Length: Approximately 58.2 mm (on average). Width: Approximately 33.1 mm (on average).
*Apex.*—Acuminate.
*Base.*—Acute.
*Margin.*—Entire, undulating.
*Shape.*—Elliptical, cupped.
*Vein color.*—About Yellow-green RHS 146A.
*Pubescence.*—Finely hairy on entire upper leaf surface, only observed along veins and midrib on lower surface.
*Arrangement on stem.*—Sub-opposite.
*Venation.*—Pinnate.
*Texture.*—Leathery. Thickness: Approximately 0.5 mm thick Degree of waxiness of surfaces: Moderately waxy.

PETIOLE

*Length.*—Approximately 1 mm.
*Shape.*—Mostly rounded to semi-oval.
*Color.*—About Yellow-green RHS 147A.
*Pubescence.*—Finely hairy.
*Diameter.*—Approximately 1 mm to 2 mm.

FLOWER BUDS

*Size.*—Length: Approximately 8 mm. Width: Approximately 7 mm.
*Color.*—About Greyed-purple RHS 184A.
*Shape.*—Rounded.
*Pubescence.*—Few fine hairs present.
*Time of full maturity.*—Mid to late June.
*Time range for showiness.*—Approximately 8 to 10 weeks.

FLOWER

Inflorescences:
*Type.*—Paniculate.
*Size.*—Length: Approximately 6 cm. Width: Approximately 8 cm.
*Color at emergence.*—About Red-purple RHS 64A.
*Color at full bloom.*—About Red-purple RHS 64A.
*Color at fading.*—About Purple RHS N79A.
*Peduncle.*—Color: About Greyed-purple RHS 183A. Pubescence: Finely hairy along edges.
Petals:
*Number.*—6.
*Size.*—Length: Approximately 18.2 mm (on average). Width: Approximately 12.4 mm (on average).
*Shape.*—Fan-shaped.
*Apex.*—Rounded.
*Base.*—Auriculate.
*Margin.*—Ruffled.
*Pubescence.*—None.
*Texture.*—Smooth.
*Color at peak of bloom.*—Upper surface: About Red-purple RHS 64A. Lower surface: About Red-purple RHS 64A.
*Pedicels.*—Color: About Greyed-purple RHS 185A. Pubescence: None. Length: Approximately 5 mm to 6 mm.

MALE REPRODUCTIVE STRUCTURES

*Number.*—Approximately 6 (fertile); approximately 30 to 40 (sterile).
*Pollen color.*—About Yellow RHS 13A.
*Pubescence.*—None.
Anther:
*Size.*—(Both fertile and sterile plants). Length: Approximately 1.5 mm. Width: Approximately 1 mm.
*Color.*—About Yellow-green RHS 144A (fertile); about Yellow-orange RHS 22A (sterile).
Filament:
*Size.*—Approximately 15 mm to 18 mm (fertile); approximately 8 mm to 10 mm (sterile).
*Color.*—About Red-purple RHS 60B (fertile); about Red-purple RHS 69B (sterile).

FEMALE REPRODUCTIVE STRUCTURES

Pistil:
*Size.*—Length: Approximately 18 mm. Width: Approximately 0.5 mm.
*Position.*—Superior.
*Pubescence.*—None.
Stigma:
*Shape.*—Rounded.
*Color.*—About Yellow-green RHS 147A.
*Pubescence.*—None.
Style:
*Length.*—Approximately 16 mm.
*Shape.*—Linear.
*Color.*—About Red RHS 46A.
*Pubescence.*—None.
Ovary:
*Shape.*—Round.
*Number.*—Approximately 1 per flower.
*Pubescence.*—None.
*Size* (*diameter*).—Approximately 2 mm.
*Color.*—About Yellow RHS 3C.

FRUIT

*Type.*—Capsule.
*Size.*—Length: Approximately 12 mm. Width: Approximately 8 mm to 10 mm.
*Color during ripening.*—Early: About Greyed-orange RHS 165B at tip; about Yellow-green RHS 146C at base. Mid: About Yellow-green RHS 146B. Late: About Black RHS 202A (before splitting); about Greyed-orange RHS 165A (after seed dispersal).
*Shape.*—Oval-rounded.
*Number per infructescence.*—Approximately 80 to 90.
*Pubescence.*—None.
*Number of carpels.*—Approximately 5.
*Persistence* (*effective period*).—Approximately 3 months.

SEED

*Shape.*—Oval-rounded.
*Size.*—Length: Approximately 6 mm. Width: Approximately 3 mm.
*Color.*—About Brown RHS 200 A (seed); about Greyed-orange RHS 164C (wing).
*Number per fruit.*—Approximately 15 to 30.
*Pubescence.*—None.

What is claimed is:

1. A new and distinct variety of crapemyrtle plant named 'Gamad VI', substantially as illustrated and described herein.

* * * * *